United States Patent
Navran, Jr.

(10) Patent No.: US 10,214,715 B2
(45) Date of Patent: Feb. 26, 2019

(54) BIOREACTOR SYSTEM FOR STEM CELL EXPANSION

(71) Applicant: Synthecon, Inc., Houston, TX (US)

(72) Inventor: Stephen S. Navran, Jr., Houston, TX (US)

(73) Assignee: Synthecon, Inc., Houston, TX (US)

( * ) Notice: Subject to any disclaimer, the term of this patent is extended or adjusted under 35 U.S.C. 154(b) by 208 days.

(21) Appl. No.: 15/129,388

(22) PCT Filed: Mar. 5, 2015

(86) PCT No.: PCT/US2015/018851
§ 371 (c)(1),
(2) Date: Sep. 26, 2016

(87) PCT Pub. No.: WO2015/153049
PCT Pub. Date: Oct. 8, 2015

(65) Prior Publication Data
US 2017/0204358 A1    Jul. 20, 2017

Related U.S. Application Data

(60) Provisional application No. 61/975,083, filed on Apr. 4, 2014.

(51) Int. Cl.
*C12M 3/00* (2006.01)
*C12M 1/00* (2006.01)
(Continued)

(52) U.S. Cl.
CPC ............ *C12M 29/10* (2013.01); *C12M 23/06* (2013.01); *C12M 25/14* (2013.01); *C12M 27/10* (2013.01);
(Continued)

(58) Field of Classification Search
CPC ...... C12M 25/14; C12M 25/02; C12M 25/06; C12M 27/18; C12M 27/22; C12M 23/06
See application file for complete search history.

(56) References Cited

U.S. PATENT DOCUMENTS

| 4,343,904 A | 8/1982 | Birch et al. |
| 5,002,890 A | 3/1991 | Morrison |

(Continued)

FOREIGN PATENT DOCUMENTS

WO    2012069841 A1    3/2012

OTHER PUBLICATIONS

(Zang) "Development of 3-D Microbioreactor Systems for Cell-Based High Throughput Screening"; P 1-258,2012; p. 80, in 11.
(Continued)

*Primary Examiner* — Nathan A Bowers
(74) *Attorney, Agent, or Firm* — Elizabeth R. Hall & Associates, P.C.; Elizabeth R. Hall (57) ABSTRACT

A bioreactor system for stem cell expansion has a fluid-filled reactor chamber in which stem cells are cultured. The culture compartment of the reactor chamber is transversed by a perfusion core with multiple niche-like scaffolds positioned along the length of the perfusion core. The bioreactor system also uses a media gas exchange module that is free standing and does not require its inclusion in a $CO_2$ incubator.

21 Claims, 6 Drawing Sheets

(51) Int. Cl.
*C12M 1/12* (2006.01)
*C12M 3/04* (2006.01)
(52) U.S. Cl.
CPC ............ *C12M 29/06* (2013.01); *C12M 29/14* (2013.01); *C12M 29/18* (2013.01); *C12M 29/20* (2013.01); *C12M 29/24* (2013.01)

(56) References Cited

U.S. PATENT DOCUMENTS

| | | | |
|---|---|---|---|
| 2004/0203140 A1* | 10/2004 | Akers | C12M 23/06 435/297.2 |
| 2008/0279441 A1 | 11/2008 | Boyan et al. | |
| 2011/0136226 A1 | 6/2011 | Navran, Jr. | |
| 2011/0207170 A1 | 8/2011 | Niazi | |
| 2014/0227769 A1* | 8/2014 | Strobbe | C12M 23/34 435/287.1 |

OTHER PUBLICATIONS

(Chaudhuri et al.) 'Bioreactors for Tissue Engineering' Dept. of Chemical Engineering; University of Bath, Bath UK 2005, p. 25, 29; FIG7b.
International Search Report dated Jul. 13, 2015 for related PCT patent application No. No. PCT/US2015/018851.

* cited by examiner

BIOREACTOR SYSTEM FOR STEM CELL EXPANSION

CROSS REFERENCE TO RELATED APPLICATIONS

This application claims priority to U.S. Patent Application Ser. No. 61/975,083 filed Apr. 4, 2014 by inventor Stephen S. Navran, Jr. entitled "Bioreactor System." The entire text of the above-referenced disclosure is incorporated by reference herein.

STATEMENT AS TO FEDERALLY SPONSORED RESEARCH

This invention was made with government support under SBIR Grant Number R44HD058391 awarded by NIH. The government has certain rights in the invention.

BACKGROUND OF THE INVENTION

Field of the Invention

The present invention relates to a method and apparatus for improving the expansion of stem cell populations. More particularly, the present invention relates to a new bioreactor and method for expanding mesenchymal stem cells in culture.

Description of the Related Art

Mesenchymal stem cells (MSCs) are adult stem cells traditionally found in the bone marrow. However, MSCs can also be isolated from other tissues including adipose tissue, umbilical cords, placenta, and dental pulp. Preliminary experimental results indicate that adult mesenchymal stem cells (MSCs) may provide therapeutic and/or regenerative benefits in the treatment of certain diseases. Such results have fueled a considerable excitement in the scientific and health communities regarding the potential of stem cells to treat a number of disease states. In fact, there are a number of clinical trials currently in progress in an effort to ascertain the true therapeutic potential of MSCs.

Originally the scientific community thought that the therapeutic benefits of MSCs resulted from the engraftment and differentiation of MSCs to replace diseased cells. However, subsequent data indicates that the beneficial effects of MSCs occur without evidence of engraftment. Rather, it has been shown that MSCs enhance tissue repair through secretions and cell-to-cell contacts (Prockop D. J. "Repair of tissues by adult stem/progentor cells (MSCs): Controversies, myths and changing paradigms", Mol. Ther. 17: 939-946, 2009; Sotiropoulou P. A., et al. "Interactions between human mesenchymal stem cells and natural killer cells", Stem Cells 24: 74-85, 2006).

A major problem in the successful clinical use of MSCs, as compared to pluripotent stem cells, is that MSCs have a low capacity to replicate ex vivo and must be continuously harvested from donors and expanded in culture to produce enough cells for therapeutic applications. In addition, as MSCs are passaged, they undergo a change in phenotype and diminished therapeutic efficacy (Izadpanah R., et al. "Long-term in vitro expansion alters the biology of adult mesenchymal stem cells", Cancer Res. 68: 4229-4238, 2008). The differentiation and diminished efficacy of passaged MSCs continues to impose severe limits on the ex vivo expansion of therapeutically potent MSCs.

Problems with the self renewal of stem cells in culture are apparently related to the fact that the conventional cell culture environment does not resemble the in vivo environment in which the stem cells normally exist. In vivo, stem cells are maintained in a largely quiescent state. Most cell divisions lead to the production of a stem cell and a daughter cell which will continue to divide to eventually produce a tissue. The numbers of stem cells actually change very little. This situation is thought to have evolved to minimize the possibility of mutations which could lead to uncontrolled growth or cancer.

Currently, the commercial expansion of MSCs is done in multilevel modules such as the Nunc® Cell Factory™ or the Corning HYPERStack®. These devices are merely high surface area analogs of standard tissue culture flasks. While these multilevel modular devices are capable of growing a large numbers of MSCs, they do not prevent the differentiation and diminished efficacy normally seen in culturally expanded MSCs. However, recent studies have shown an enhanced therapeutic potency for MSCs cultured in three dimensions as compared to MSCs expanded using conventional two dimensional culture systems (Frith, J. E., et al. "Dynamic three-dimensional culture methods enhance mesenchymal stem cell properties and increase therapeutic potential", Tissue Eng. Part C Methods 16: 735-749, 2010). This reported improvement in therapeutic potential is likely due to the increased secretion of paracrine factors and the reduced cell size which permits infused MSCs to migrate to an injury site through the smallest arterioles (Bartosh, T. J., et al. "Aggregation of human mesenchymal stromal cells (MSCs) into 3D spheroids enhances their antiinflammatory properties", Proc. Natl. Acad. Sci. (USA) 107: 13724-13729, 2010).

It has been proposed that culturing MSCs in three dimensional culture systems more closely resembles the in vivo microenvironment, or niche, of these cells than the two dimensional systems. Simulating the normal microenvironment of the cells in vivo is thought to be a critical factor in maintaining the MSC phenotype and therapeutic potential during cell expansion (Cheng, N-C, et al. "Short-Term Spheroid Formation Enhances the Regenerative Capacity of Adipose-Derived Stem Cells by Promoting Stemness, Angiogenesis and Chemotaxis", Stem Cells Translational Med. 2: 584-594, 2013).

An ongoing problem in the three dimensional culturing of MSCs is that there are no successful large-scale commercial MSC culturing systems available. All of the initial work done on three dimensionally cultured MSCs has been done using spheroids produced by hanging drop culture or hydrogel encapsulated cells, techniques which are inherently limited in the scale of MSC production. Thus, a continuing need exists for improving three dimensional culture systems for the large scale expansion of stem cells.

SUMMARY OF THE INVENTION

Embodiments of the present invention include a method and apparatus for improving the expansion of stem cell populations. Embodiments of the bioreactor system of the present invention include a fluid-filled reactor chamber in which stem cells are cultured. The culture compartment of the reactor chamber is transversed by a perfusion core with multiple niche-like scaffolds positioned along the length of the perfusion core.

One embodiment of the present invention is a cell culture system comprising: (a) a bioreactor chamber having a sleeve, an inlet cap mounted on a first end of the sleeve and an outlet cap mounted on a second end of the sleeve; (b) a porous perfusion core having a central bore with an impermeable plug positioned within the central bore, wherein the perfusion core transverses a longitudinal axis of the culture chamber; (c) a porous scaffold having a central aperture, wherein the central apertures of a plurality of scaffolds are threaded over an external surface of the perfusion core to align the scaffolds along a length of the perfusion core; (d) a media gas exchange module; (e) a pump; (f) a first tubing connecting an outlet of the bioreactor chamber to the inlet of the media gas exchange module; and (g) a second tubing connecting an inlet of the bioreactor chamber to the outlet of the media gas exchange module.

Another embodiment of the present invention is a bioreactor chamber comprising: (a) a cylindrical sleeve with a hollow core; (b) an inlet cap mounted on a first end of the sleeve having an inlet nozzle centrally mounted on an exterior surface of the inlet cap, wherein a through bore of the inlet nozzle passes through the inlet cap to the hollow core of the sleeve; (c) an outlet cap mounted on a second end of the sleeve having an outlet nozzle centrally mounted on an exterior surface of the outlet cap, wherein a through bore of the outlet nozzle passes through the outlet cap to the hollow core of the sleeve; (d) a porous perfusion core having a central bore axially aligned with the through bore of the inlet nozzle and the through bore of the outlet nozzle, wherein an impermeable plug is positioned within the central bore dividing the central bore into a first inlet segment and a second outlet segment; and (c) a porous scaffold having a central aperture, wherein the central apertures of a plurality of scaffolds are threaded over an external surface of the perfusion core to align the scaffolds along a length of the perfusion core.

Yet another embodiment of the present invention is a media gas exchange module comprising: (a) a canister; (b) a spindle mounted within the canister; (c) a gas inlet port; (d) a gas outlet port; (e) a gas exchange tubing wrapped around the spindle and connected at a first end to the gas inlet port and at a second end to the gas outlet port; (f) a media inlet; and (g) a media outlet.

One aspect of the invention is a cell culture process comprising: (a) filling a bioreactor chamber with a tissue culture media, wherein the bioreactor chamber has (i) a tubular sleeve sealed at each end with an end cap, wherein each end cap has a through bore passing through the end cap into a hollow core of the sleeve, (ii) a porous perfusion core transversing a longitudinal axis of the sleeve, wherein the perfusion core has a central bore with an impermeable plug positioned within the central bore that divides the central bore into a first inlet segment and a second outlet segment and wherein the central bore of the perfusion core is aligned with the through bore of each end cap, and (iii) a porous scaffold having a central aperture, wherein the central apertures of a plurality of scaffolds are threaded over an external surface of the perfusion core to align the scaffolds along a length of the perfusion core within the hollow core of the sleeve; (b) incubating the media filled bioreactor chamber at 37° C.; (c) pumping the media through the bioreactor chamber by pumping the media from an inlet of the bioreactor chamber to the first inlet segment, out through a wall of the perfusion core surrounding the first inlet segment, between the scaffolds, around a periphery of the scaffold, through the wall of the perfusion core into the second outlet segment, and out through an outlet of the bioreactor chamber; (d) circulating the media from the outlet of the bioreactor chamber to a media gas exchange module and back into the inlet of the bioreactor chamber; (e) stopping the flow of media into the bioreactor chamber for 24 hours; (f) introducing multiple suspended stem cells into the bioreactor chamber; (g) rotating the bioreactor chamber; and (h) restarting the circulation of media through the bioreactor chamber and the media gas exchange module.

Yet another aspect of the present invention is a process for expanding stem cells in culture comprising: (a) filling a bioreactor chamber with a tissue culture media, wherein the bioreactor chamber has (i) a tubular sleeve sealed at each end with an end cap, wherein each end cap has a through bore passing through the end cap into a hollow core of the sleeve, (ii) a porous perfusion core transversing a longitudinal axis of the sleeve, wherein the perfusion core has a central bore with an impermeable plug positioned within the central bore that divides the central bore into a first inlet segment and a second outlet segment and wherein the central bore of the perfusion core is aligned with the through bore of each end cap, (iii) a disk shaped scaffold having a central aperture and numerous pores of various sizes that penetrate the scaffold, wherein the central apertures of a plurality of scaffolds are threaded over an external surface of the perfusion core to align the scaffolds along a length of the perfusion core within the hollow core of the sleeve, and (iv) a penetration port mounted in the sleeve or in one of the end caps; (b) incubating the media filled bioreactor chamber at 37° C.; (c) pumping the media through the bioreactor chamber by pumping the media from an inlet of the bioreactor chamber to the first inlet segment, out through a wall of the perfusion core surrounding the first inlet segment, between the scaffolds, around a periphery of the scaffolds, through the wall of the perfusion core into the second outlet segment, and out through an outlet of the bioreactor chamber; (d) circulating the media from the outlet of the bioreactor chamber to a media gas exchange module and back into the inlet of the bioreactor chamber; (d) stopping the flow of media into the bioreactor chamber for 24 hours; (e) introducing multiple suspended stem cells into the bioreactor chamber through the penetration port; (f) rotating the bioreactor chamber; and (g) restarting the circulation of media through the bioreactor chamber and the media gas exchange module.

The foregoing has outlined several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiments disclosed might be readily utilized as a basis for modifying or redesigning the method or process for carrying out the same purposes as the invention. It should be realized that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Embodiments of the invention include a scalable commercial cell culturing system. Preferred embodiments of the invention include a bioreactor system for stem cell expansion having a fluid-filled reactor chamber in which stem cells are cultured, preferably human MSCs. The culture compartment of the reactor chamber is transversed by a perfusion core with multiple niche-like scaffolds positioned along the length of the perfusion core Referring now to the drawings, and initially to FIG. 1, it is pointed out that like reference characters designate like or similar parts throughout the drawings. The Figures, or drawings, are not intended to be to scale. For example, purely for the sake of greater clarity in the drawings, wall thickness and spacing are not dimensioned as they actually exist in the assembled embodiments.

Figure 1:
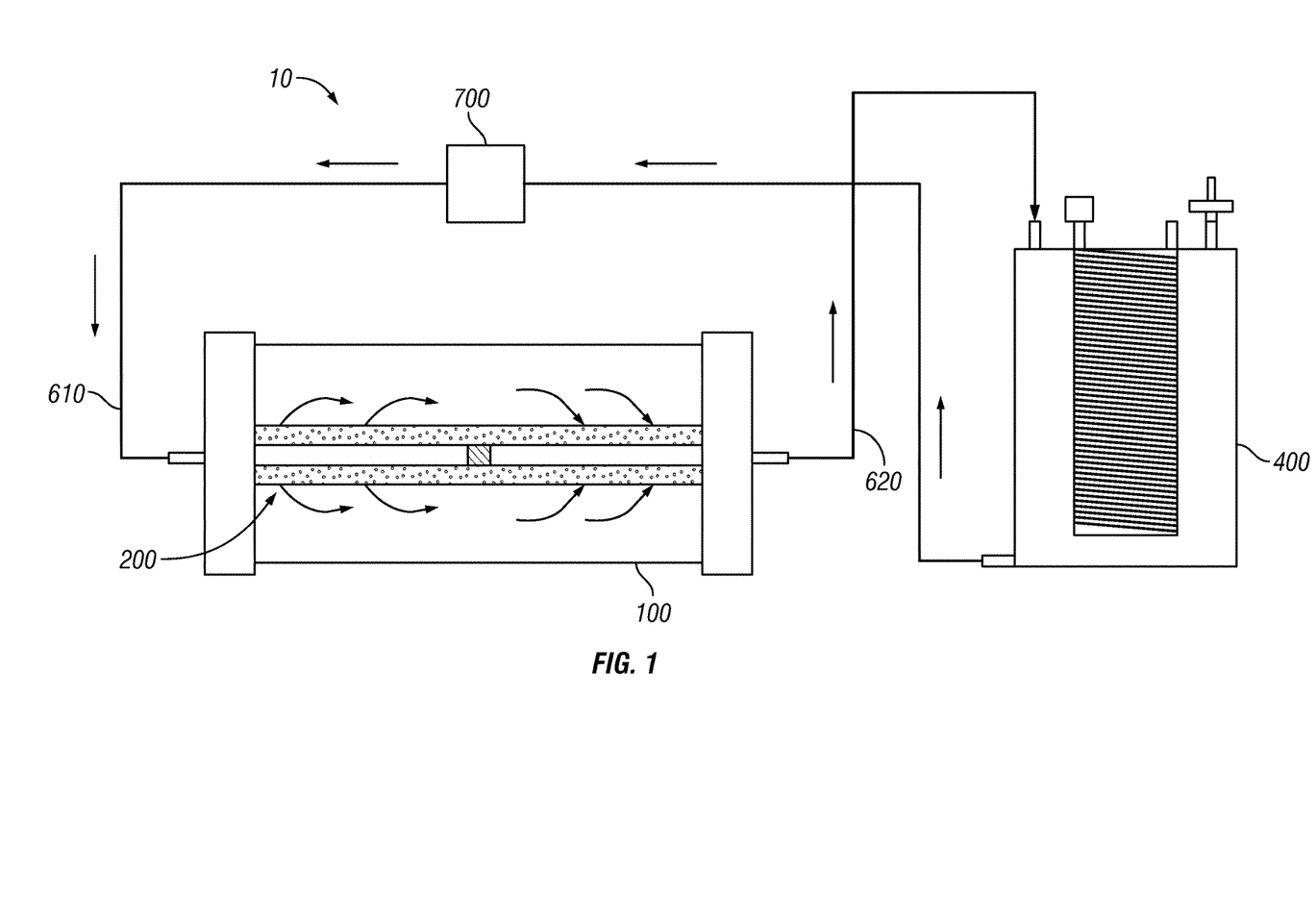
FIG. 1 is a schematic representation of the bioreactor system without the niche-like scaffolds mounted along the length of the perfusion core.
Figure 8:
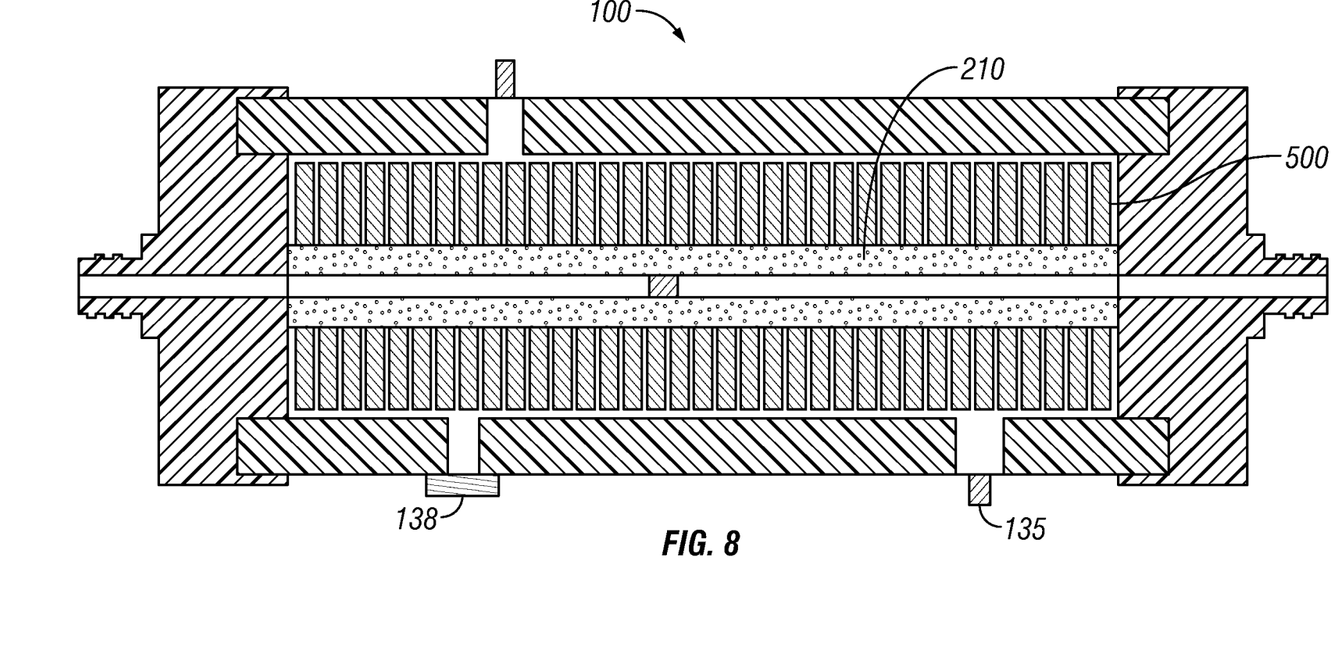
FIG. 8 is a cross sectional view of the reactor chamber assembled with the niche-like scaffolds mounted along the length of the perfusion core.

FIG. 1 is a schematic representation of a preferred embodiment of a basic bioreactor system 10 used for the expansion of MSCs without the niche-like scaffold positioned along the perfusion core. The bioreactor system 10 includes a rotating reactor chamber 100, as shown in FIG. 8, with a sleeve 130 and two end caps that enclose a culture chamber 150. The culture chamber 150 is transversed by a perfusion core 200 having multiple niche-like scaffolds 500 positioned along the length of the perfusion core 200. The perfusion core 200 has a central bore 220 with a plug 230 located along the length of the central bore that separates the central core into a first inlet segment 250 and a second outlet segment 260.

Reactor Chamber

Figure 2:
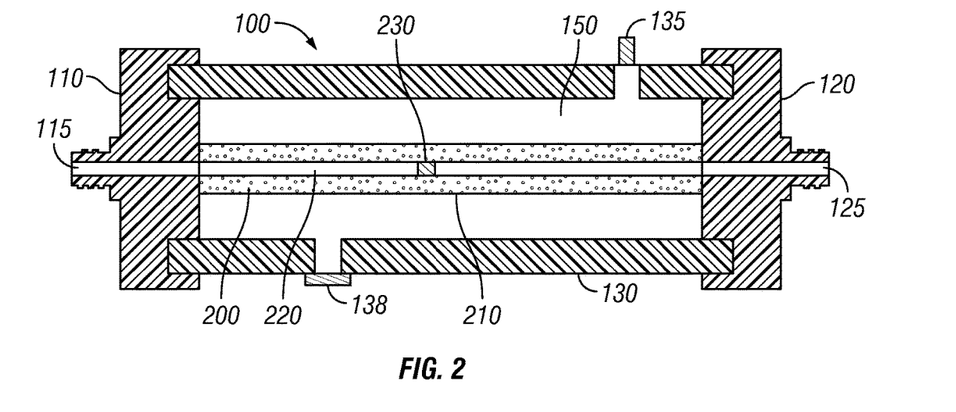
FIG. 2 is a cross sectional view of the reactor chamber without the niche-like scaffolds mounted along the length of the perfusion core.

One embodiment of the reactor chamber 100 is shown in FIG. 2. In this embodiment, the reactor chamber 100 is constructed for horizontal rotation. The rotating reactor chamber 100 simulates the effects of microgravity by maintaining cells in suspension at very low shear stress (0.8 dynes/cm$^2$) with high diffusion rates of oxygen, nutrients and waste. The culture chamber 150 is completely filled with media to avoid a headspace which can create cell-damaging bubbles and turbulence.

The reactor chamber 100 is designed to be supported on and rotated by a roller drive that rotates the reactor chamber about its axis. Thus, the reactor chamber 100 is typically cylindrical in construction. The reactor chamber has a tubular sleeve 130 with a hollow core. The sleeve 130 is sealed at each end with similar end caps, the inlet end cap 110 and the outlet end cap 120, so that a sealed growth compartment or culture chamber 150 is formed within the enclosed space between end caps 110 and 120, the interior of sleeve 130, and around the perfusion core 200.

The inlet end cap 110 has an inlet nozzle 115, also referred to as the inlet. The inlet nozzle is centrally mounted on an exterior surface of the inlet cap 110. The inlet nozzle has a through bore that passes through the inlet 115 and the inlet cap 110. Likewise, the outlet end cap 120 has an outlet nozzle 125, also referred to as the outlet. The outlet nozzle is centrally mounted on an exterior surface of the outlet cap 120. The outlet nozzle has a through bore that passes through the outlet nozzle 125 and the outlet cap 120.

Figure 3:
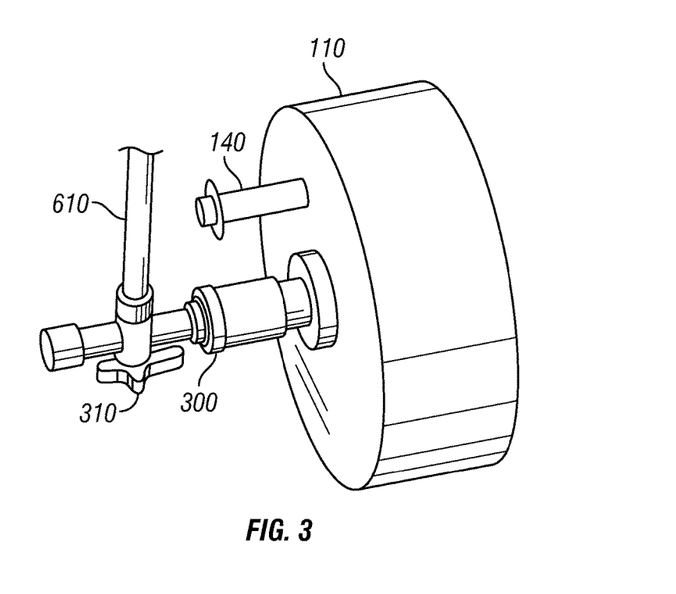
FIG. 3 is an oblique view of an end cap of the reactor chamber shown in FIG. 2.
Figure 4:
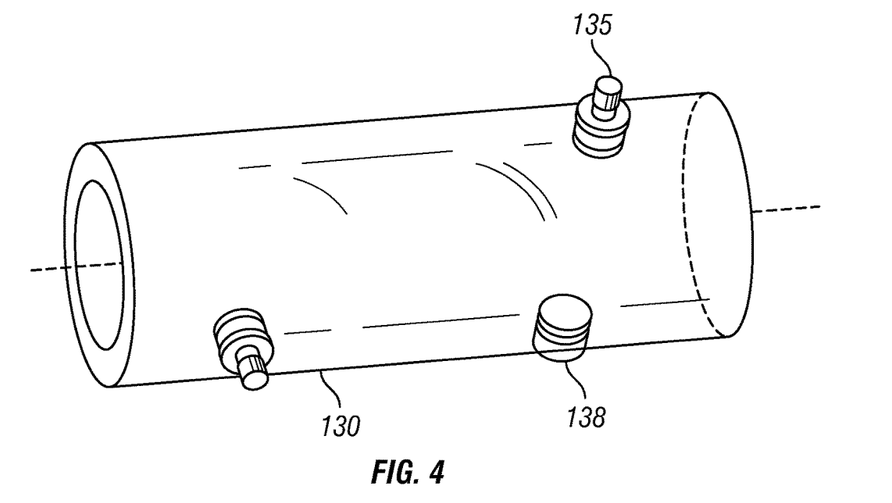
FIG. 4 is an oblique view of the sleeve of the reactor chamber.

Fluid-conducting swivels 300, stopcock valves 310, and fluid inlet tubing 610 and outlet tubing 620 are provided on the end caps 110, 120 of the reactor chamber 100 so that the nutrient fluid and its attendant waste fluid may be delivered and controlled. As shown in FIGS. 3 and 4, one or more penetration ports 135, 140, and 138 are provided in either the wall of sleeve 130 or in one of the end caps 110, 120. For example, sampling port 138 is used for inserting fluids and cells into or removing fluids and cells from the interior of the culture chamber 150 while the reactor chamber 100 is in service but not rotating. Fill ports 135 and 140 are used to add or remove liquids or media.

Perfusion Core

The reactor chamber 100 is transversed along its longitudinal axis with a perfusion core 200. The perfusion core 200, illustrated in FIGS. 2 and 5, may be made of any solid porous material. A preferred embodiment of the perfusion core 200 is made of highly porous high density polyester having pore sizes of 20-60 μm. The perfusion core 200 has a central bore 220 that is aligned with the through bore of the inlet nozzle 115, the inlet end cap 110, the outlet end cap 120, and the outlet nozzle 125.

Figure 5:
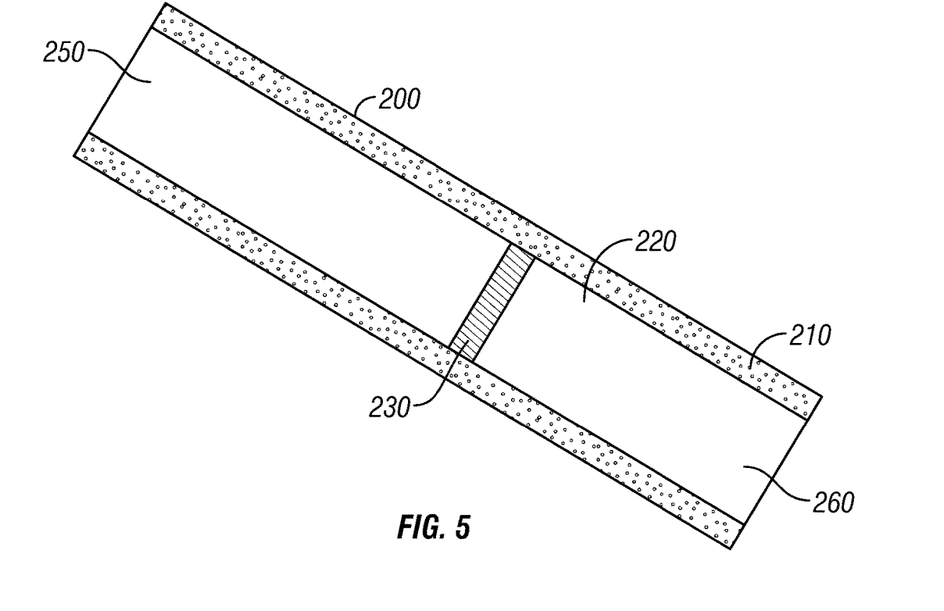
FIG. 5 is a cross sectional view of the perfusion core.

A solid impermeable plug 230 is placed along the length of the central bore 220 to divide the central bore into a first inlet segment 250 and a second outlet segment 260. The impermeable plug 230 may be positioned at the center of the central bore 220 midway between the inlet 115 and the outlet 125, or it may be placed at any position along the length of the central bore 220. Preferably the solid plug 230 is placed either in the center of the central bore 220 or closer to the outlet 125 than to the inlet 115. The solid plug forces the flow of media through the pores of the perfusion core on the inflow side and allows the media to re-enter the central bore 220 on the outflow side. This arrangement provides a more even distribution of media throughout the culture chamber 150.

A schematic diagram of the media circulation system is shown in FIG. 1. Basically, the media passes from the inlet 115 of the reactor chamber into the first inlet segment 250 of the central bore 220 in the perfusion core 200. As the media passes along the central bore of the porous perfusion core, it diffuses outwardly into the culture chamber 150. When the media reaches the plug in the central bore, the media is pushed outward through the perfusion core into the culture chamber 150. The media circulating through the culture chamber must then reenter the second outlet segment 260 of the central bore 220 of the perfusion core 200 in order to pass out of the outlet 125 of the reactor chamber. Once the media has passed through the reactor chamber 100, the media is pumped by a peristaltic pump 700 through a gassing module 400 and then back to the inlet 115 of the reactor chamber 100.

Niche-Like Scaffold

In addressing the problems associated with stem cell expansion, the role of the microenvironment or stem cell niche has become evident (Scadden, D. T. "The stem cell niche as an entity of action", Nature 441: 1075-1079, 2006). The stromal or mesenchymal stem cells (MSCs) first discovered in the bone marrow provide a rich environment of soluble factors, extracellular matrix and adhesion molecules that regulate the balance between self renewal and differentiation of stem cells (Yamashita, Y. M., et al. "Signaling in stem cell niches: lessons from the Drosophilia germline", J. Cell Sci. 118: 665-672, 2005).

Because stem cells are normally maintained within the niche in a quiescent state, it is not surprising that attempts to expand them for therapeutic applications in conventional culture systems have met with little success. As many investigators have pointed out, the existence of a population of cells with unlimited growth potential, requires stringent control of proliferation to prevent the emergence of cancerous cells, a function which has been proposed for the stem cell niche (Li, L. and Neaves, W. B. "Normal stem cells and cancer stem cells: the niche matters", Cancer Res. 66: 4553-4557, 2006; Chepko, G., et al. "Differential alteration of stem and other cell populations in ducts and lobules of TGFα and c-Myc transgenic mouse mammary epithelium", Tissue Cell 37: 393-412, 2005).

Culturing MSCs in three dimensions enhances the therapeutic potency of MSCs as compared to conventional two dimensional culture methods. Unfortunately, the current methods of establishing three dimensional cultures in the laboratory are not scaleable for commercial production. Desirable criteria for large scale therapeutic MSC expansion are: (a) high surface area to volume ratio, (b) closed system to minimize the risk of contamination, (c) simple seeding and harvesting, (d) economical running costs, and (e) a smaller footprint than conventional three dimensional systems.

Figure 6:
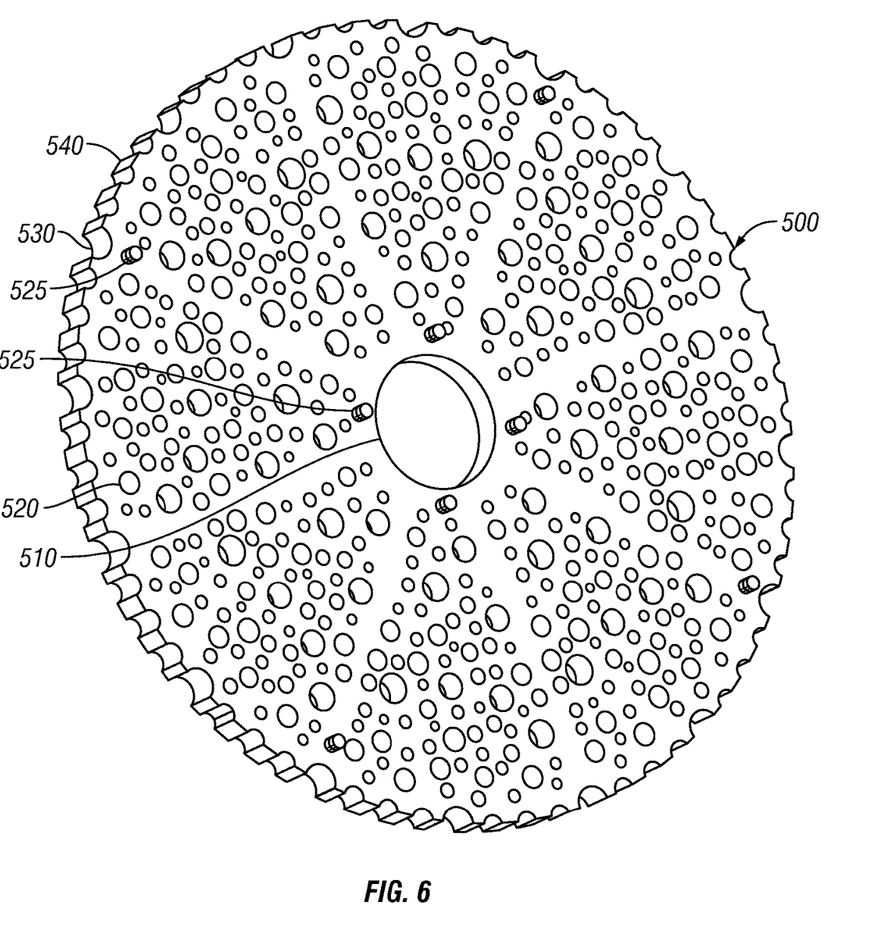
FIG. 6 is a pan view of the niche-like scaffold.

Preferred embodiments of the bioreactor system 10 will have a plurality of solid scaffolds for providing a surface area for the adherence of MSCs. Embodiments of the scaffold 500 will have the structure of a porous mesh similar to the bone marrow niche where the MSCs reside in vivo. One embodiment of the scaffold 500 is illustrated in FIG. 6. The scaffold 500 will be produced as a disk with the structure of a porous mesh. The scaffold will be highly porous to provide a large surface area to volume ratio allowing the adherence and growth of large numbers of cells in a three dimensional environment with a very small footprint compared to currently used two dimensional and three dimensional culture systems.

The scaffold disks can be made by any of several methods such as solvent casting/particulate leaching, emulsion freeze drying, gas foaming electrospinning or injection molding. The disks will be manufactured using biocompatible materials. Several materials are know to be biocompatible in the culturing of MSCs, such as poly(lactic-co-glycolic) acid, polycaprolactone, alginate, hydroxyappatite and polystyrene. These materials may also be chemically modified to bind or be coated with naturally occurring extracellular proteins or peptides to enhance cell adhesion.

Each disk 500 will be produced with an aperture 510 in the center of the disk that has a diameter that is slightly greater than the diameter of the perfusion core 200. Preferably, the circumference of the aperture 510 is 1% to 7% longer than the circumference of the external surface of the perfusion core 200. Typically, when the scaffold disks 500 are threaded over the external surface of the perfusion core it is a snug fit.

In addition, each disk 500 will have a number of openings 520 of various sizes that penetrate the disk to increase its surface area. The diameter of the disk is similar to but slightly smaller than the internal diameter of the reactor chamber so that the disk will easily fit within the reactor chamber 100. Typically, the diameter of the disk 500 will equal about 85% to 99% of the internal diameter of the sleeve 130. Furthermore, the width of the disk will be significantly less than the diameter of the disk (e.g., from about 1% to about 10% the diameter of the disk).

One embodiment of the disk 500 will have multiple concavities 530 spaced along the length of its perimeter 540. The disk 500 may optionally include one or more small protrusions 525 extending outwardly from a surface of the disk.

Bioreactor System

FIG. 1 is a schematic representation of a preferred embodiment of a basic bioreactor system 10 used for the expansion of MSCs without the niche-like scaffold positioned along the perfusion core. The bioreactor system 10 includes a horizontally rotating, zero head space reactor chamber 100. The reactor chamber includes a tubular sleeve 130 sealed at each end with similar end caps. The sleeve encircles a culture chamber 150.

The culture chamber 150 is transversed by a liquid-permeable perfusion core 200 having a central bore 220 with a solid plug 230 located along the length of the central bore that separates the central core into a first inlet segment 250 and a second outlet segment 260.

When the bioreactor chamber 100 is assembled the central aperture 510 of each scaffold 500 is threaded over the external surface of the perfusion core 200. Numerous scaffold disks are lightly packed along the length of the perfusion core. Each disk 500 will optionally include one or more small protrusions 525 extending outwardly from a surface of the disk to ensure that there is a small distance between the packed disks on the central perfusion core 200 of the bioreactor chamber to facilitate the flow of media between the disks (see FIG. 8). The concavities 540 along the periphery of the disk 500 will also facilitate media flow within the culture chamber 150.

The arrows in FIG. 1 illustrate the circulation of media throughout the bioreactor system 10. The media enters the inlet 115 of the reactor chamber 100 and exits the outlet 125 of the reactor chamber. The media passes from the inlet of the reactor chamber into the first inlet segment 250 of the central bore in the perfusion core 200. As the media passes along the central bore 220 of the porous perfusion core, it diffuses outwardly into the culture chamber 150. When the media reaches the plug 230 in the central bore, the media is diverted outward through the perfusion core into the culture chamber 150 so that the media will be directed radially through the niche-like scaffolds 500. The media circulating through the culture chamber must then reenter the second outlet segment 260 of the central bore of the perfusion core in order to exit the outlet 125 of the reactor chamber. Once the media has passed through the reactor chamber 100, the media is sent through a gassing module 400 and then back through the flow loop to the inlet 115 of the reactor chamber.

The majority of the interior of the culture chamber 150 is filled with niche-like scaffolds 500 mounted along the length of the perfusion core 200 (e.g., from about 60% to about 90% of the area of the core of the sleeve). In addition to the scaffold which simulates the natural MSC niche, it is also important that the culture system mimic the physiological conditions of the circulatory system (e.g., the supply of nutrients and $O_2$ and the maintenance of a physiological pH). The conventional static culture systems that are currently in use are inadequate at maintaining consistent culture conditions. Even stirred systems which have good mass transport, introduce damaging shear stress. To provide the proper gas exchange for the expanding MSCs without subjecting the cells to turbulence, the bioreactor system will include a gas module 400 that delivers the appropriate gas mixture directly into a media filled reservoir. This will allow the bioreactor system 10 to be scaled up, since it will not be restricted to a $CO_2$ incubator.

Media Gas Exchange Module

Conventional tissue culture techniques grow cells in culture chambers within a gas filled incubator. Similarly, all currently used rotating culture chambers perform the requisite gas exchange by circulating the media through coiled silicone tubing exposed to the ambient gas mixture inside an incubator. Embodiments of the present invention do not use the typical oxygenator assembly, but have the gas exchange take place in an external media gas exchange module 400, illustrated in FIGS. 1 and 7.

Figure 7:
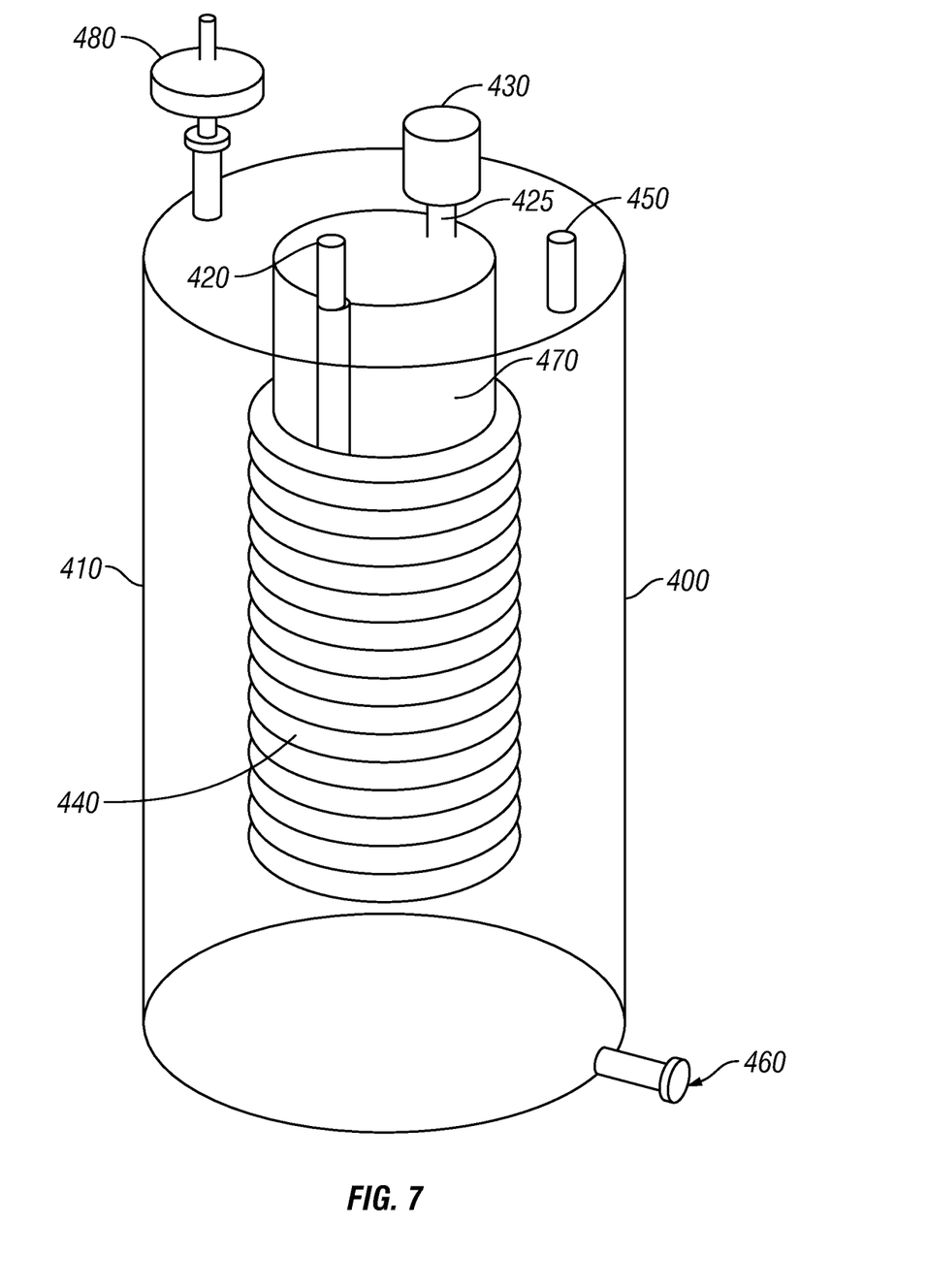
FIG. 7 is a pan view of the media gas exchange module.

The media gas exchange module 400 shown in FIG. 7 includes a canister 410 where the canister has a top surface with a media inlet 450 mounted on the top surface. The canister 410 also has a bottom surface with the media outlet 460 mounted on the canister proximal the bottom surface.

The gas exchange module 400 has a gas exchange tubing 440 wrapped around the spindle 470 positioned within the canister 410. The gas exchange tubing is wrapped about a majority of the external surface of the spindle 470 to provide a large gas exchange surface between the gas exchange tubing and the media that fills the canister 410. Preferably, the module will provide 1-4 cm$^2$ of gas exchange tubing surface area for every milliliter of media in contact with the gas exchange tubing surface area. A first end of the gas exchange tubing 440 is attached to a gas inlet port 420, the gas exchange tubing is wrapped around the spindle 470 positioned with the canister, and a second end of the gas exchange tubing is attached to a gas outlet port 425 having a pop-up valve 430 with a preselected escape pressure.

Tissue culture media is pumped into the canister 410 of the media gas exchange module 400 through the media inlet 450 until the media fills the canister 410 around the gas exchange tubing 440. Once the canister is filled with media, the media will pass out the media outlet 460. The gas inlet port 420 is then connected to a tank of gas containing $O_2$, $CO_2$, and $N_2$ in the desired proportions. The gas pressure on the tank is adjusted to be just below the escape pressure of the pop-up valve 430.

When the gas pressure within the media gassing module 400 has been adjusted to the desirable pressure, the gas will be slowly driven into the media without the development of bubbles in the media. Avoiding the bubbling of the media, the tissue culturist avoids the denaturation of the proteins within the tissue culture media. A pressure relief valve 480 is mounted on the top surface of the canister 410 distal to the medial inlet 450 to allow any excess gas mixture to escape the interior of the media gas exchange module if the gas pressure in the module surpasses the desired pressure.

The tissue culture media is circulated through the media gas exchange module 400 to perform the desired gas exchange. The media outlet 460 is connected to a pump 700 by the fluid inlet tubing 610 which pulls media from the media gas exchange module 400 and circulates the media through the rotating reactor chamber 100. Once the media has passed through the bioreactor chamber, the media is returned to the media gassing module via the fluid outlet tubing 620 into the media inlet 450.

The media gas exchange module allows the proper gas mixture to be injected directly into the tissue culture media without the requirement of an expensive $CO_2$ incubator. The use of a stand alone media gas exchange module allows the bioreactor to be scaled up beyond the size constraint of an incubator Operation of the Bioreactor System Seeding the MSCs Highly porous scaffolds present problems for seeding efficiency in conventional cell culture systems. In static systems, most of the cells fall through the pores and accumulate on the bottom of the culture vessel rather than attaching to the scaffold. In stirred or sparged systems, the mechanical forces used to keep the cells in suspension limit the attachment of the cells to the scaffold. The bioreactor system addresses these problems by suspending the seeded cells in a low shear force environment using horizontal rotation of the culture vessel. The suspension of the cells and their access to the scaffold surface under low shear forces promotes the efficient attachment of cells to the scaffold 500.

The reactor chamber 100 will be filled with media ($\alpha$-MEM, 20% FBS, 1 mM pyruvate, penicillin, and streptomycin) and vented to ensure that there is a zero-head space in the reactor chamber. The filled reactor chamber 100 will be incubated at 37° C. and the media pumped through the media gas exchange module 400 having its gas exchange tubing 440 filled with a gas mixture of 5% $CO_2$, 5% $O_2$, and 90% $N_2$.

The bioreactor cell culture system 10 is scalable for commercial production of viable cells. Preferred embodiments have been optimized for the expansion of stem cells, particularly human MSCs. Human MSCs obtained from Stem Cell Technologies will initially be cultured from frozen stocks in a T75 flask, trypsinized and introduced into the bioreactor chamber 100 through a port 135, 138, 140 in an end cap or in the wall of the sleeve 130. Typically, the MSCs will be introduced into the bioreactor chamber through a sampling port 138. The vessel will be slowly rotated without media flow for 24 hours to allow an opportunity for the MSCs to efficiently seed the scaffold 500 surface. In a suspension culture, MSCs readily attach to the scaffolds 500 at rotational speeds between 1-7 rpm. After 24 hours, the media flow will be initiated and a sample of the media in the culture chamber 150 will be taken and the number of unattached cells will be counted to assess the seeding efficiency of the MSCs to the scaffolds 500.

Harvesting the MSCs

To harvest MSCs, the media will be gently washed out of the reactor chamber with PBS and drained from the vessel through a port 135, 138, 140. An enzyme solution that is a mixture of proteolytic and collagenolytic enzymes extracted from crustaceans obtained from Invitrogen (i.e., Accutase®) will be perfused through the reactor chamber to gently remove the attached cells without damaging the surface markers. The detached cells are collected through a sampling port 138, washed and assess for their therapeutic viability and proliferative capacity as described below.

Assessing the Therapeutic Viability and Proliferative Capacity of the Expanded MSCs The therapeutic viability and proliferative capacity of the MSCs expanded in the bioreactor system will be assessed before the expanded cells are used clinically. The cell size, cell number, the clonogenicity, the immunophenotype, and the secretory activity of harvested expanded MSCs will be compared to the same parameters of statically expanded MSCs. Preferably, only the expanded MSCs harvested from the bioreactor system 10 that show a statistically significant improvement (i.e., $P \leq 05$) in the number of cell doublings that maintain the immunophenotype of viable MSCs and/or a statistically significant increase in their immunomodulary secretions as compared to those parameters in statically expanded MSCs will be approved for clinical use.

Control MSC cultures will be seeded in T75 flasks. The cultures in the T75 flasks will be passaged at 70-80% confluence. MSCs harvested from this static two dimensional culture system will be compared to MSCs harvested from the bioreactor system 10. All harvested cell samples will be characterized as follows.

1. Cell Number and Size.

MSCs harvested by enzyme treatment will be counted using a Millipore™ Scepter™ automated cell counter. In addition, a distribution of cell size will be obtained by this instrument as cell size is an important therapeutic indicator (smaller cells are better able to home to sites of injury than larger cells).

2. Clonogenicity.

The ability of MSCs to form colonies has also been shown to be a good predictor of proliferative capacity. Colony-forming assays (CFU) will be performed on each group of harvested cells to assess the capability of the bioreactor to sustain MSC proliferative capacity as compared to the static 2D culture system.

3. Immunophenotype.

Therapeutically viable MSCs have been characterized by the expression of a number of surface markers including CD73, CD90, CD105 and Stro-1 with the absence of hematopoietic markers. Showing that the cultured MSCs maintain their expression of these surface markers is an indicator of their sustained multipotency. The immunophenotype of each group of harvested cells, from the bioreactor system or from the T75 flasks, will be determined by immunostaining the cells with labeled antibodies (obtained from BD Biosciences) to C73, CD90, CD105 and CD45, Stro-1 and appropriate isotype controls. The immunostained cells will be analyzed with a guava EasyCyte™ flow cytometer running guavaSoft 2.0 software.

4. Secretory Activities.

Recent clinical trials using MSCs have shown that their therapeutic efficacy is related to their immunomodulatory capability and their secretion of certain soluble factors. Since it has been reported that culturing MSCs in 3D culture systems significantly enhance MSC secretions as compared to static 2D culture systems, MSCs cultured in the bioreactor system and in the T75 flasks will be tested for their secretion of several immunomodulatory factors, including prostaglandin $E_2$ ($PGE_2$), hepatocyte growth factor (HGF), and TGF-β1(stimulated by IFN-γ). An analysis of the secretion of these factors will be tested on an equal number of MSCs harvested from both 2D and 3D bioreactor cultures. Each culture sample will be seeded in 6 well plates and cultured for 24 hours. After a 24 hour incubation, the media will be analyzed by ELISAs for $PGE_2$, HGF and TGF-β1 (obtained from R&D Systems).

The foregoing provides a detailed description of the invention which forms the subject of the claims of the invention. It should be appreciated by those skilled in the art that the general design and the specific embodiments disclosed might be readily utilized as a basis for modifying or redesigning the bioreactor system to perform equivalent functions, but those skilled in the art should realize that such equivalent constructions do not depart from the spirit and scope of the invention as set forth in the appended claims.

What is claimed is:

1. A cell culture system comprising:
   (a) a bioreactor chamber having a sleeve, an inlet cap mounted on a first end of the sleeve and an outlet cap mounted on a second end of the sleeve;
   (b) a porous perfusion core having a central bore with an impermeable plug positioned within the central bore, wherein the perfusion core transverses a longitudinal axis of the culture chamber;
   (c) a plurality of porous scaffolds, each having a protrusion extending outwardly and a central aperture, wherein the scaffold is a biocompatible disk having a plurality of concavities spaced along a circumference of the disk, wherein the central apertures of a plurality of scaffolds are threaded over an external surface of the perfusion core to align the scaffolds along a length of the perfusion core, wherein each scaffold abuts the protrusion of the adjacent scaffold to form a media channel between adjacent scaffolds;
   (d) a media gas exchange module;
   (e) a pump;
   (f) a first tubing connecting an outlet of the bioreactor chamber to the inlet of the media gas exchange module; and
   (g) a second tubing connecting an inlet of the bioreactor chamber to the outlet of the media gas exchange module.

2. The cell culture system of claim 1, further comprising a fill port and a sampling port.

3. The cell culture system of claim 1, wherein the bioreactor chamber is cylindrical and rotated by a roller drive.

4. The cell culture system of claim 1, wherein a fluid-conducting swivel and a stopcock valve are attached to the inlet and outlet of the bioreactor chamber.

5. The cell culture system of claim 1, wherein the impermeable plug divides the central bore of the porous core into a first inlet segment and a second outlet segment.

6. The cell culture system of claim 5, wherein a length of the first inlet segment is equal to or greater than a length of the second outlet segment.

7. The cell culture system of claim 5, further comprising a media circulation path passing from the inlet cap to the outlet cap wherein the media circulation path passes through the first inlet segment of the perfusion core, the media channels positioned over the first inlet segment, the core of the sleeve, the media channels positioned over the second outlet segment, the second outlet segment of the central core of the perfusion core, and the outlet cap.

8. The cell culture system of claim 1, wherein the scaffold has numerous pores of various sizes that penetrate the scaffold.

9. The cell culture system of claim 1, wherein the concavities spaced along the circumference of the disk make up at least 50% of the circumference of the disk and less than 15% of a surface area of the disk.

10. The cell culture system of claim 1, wherein the media gas exchange module includes:
    (a) a canister;
    (b) a spindle mounted within the canister;
    (c) a gas inlet port;
    (d) a gas outlet port;
    (e) a gas exchange tubing wrapped around the spindle and connected at a first end to the gas inlet port and at a second end to the gas outlet port, wherein 1-4 $cm^2$ of gas exchange tubing surface area is provided for each millimeter of media in contact with the gas exchange tubing surface area;
    (f) a pop-up valve mounted on the gas outlet port opposite the gas exchange tubing;
    (g) a media inlet; and
    (h) a media outlet.

11. A bioreactor chamber comprising:
    (a) a cylindrical sleeve with a hollow core;
    (b) an inlet cap mounted on a first end of the sleeve having an inlet nozzle centrally mounted on an exterior surface of the inlet cap, wherein a through bore of the inlet nozzle passes through the inlet cap to the hollow core of the sleeve;

(c) an outlet cap mounted on a second end of the sleeve having an outlet nozzle centrally mounted on an exterior surface of the outlet cap, wherein a through bore of the outlet nozzle passes through the outlet cap to the hollow core of the sleeve;

(d) a porous perfusion core having a central bore axially aligned with the through bore of the inlet nozzle and the through bore of the outlet nozzle, wherein an impermeable plug is positioned within the central bore dividing the central bore into a first inlet segment and a second outlet segment; and (e) a plurality of porous scaffold disks, each disk having at least one protrusion extending outwardly a first distance from a flat surface of the disk and a central aperture, wherein the central apertures of a plurality of scaffolds disks are threaded over an external surface of the perfusion core to align the scaffolds disks along a length of the perfusion core, wherein each disk abuts the protrusions of an adjacent disk to form a media channel between adjacent disks having a width substantially equal to the first distance.

12. The bioreactor chamber of claim 11, wherein the sleeve, the inlet cap, the outlet cap, or any combination of the same has at least one penetration port to provide direct access to the core of the sleeve between the sleeve and the scaffold disks.

13. The bioreactor chamber of claim 11, wherein the bioreactor is cylindrical and rotated by a roller drive.

14. The bioreactor chamber of claim 11, wherein a length of the first inlet segment is equal to or greater than a length of the second outlet segment.

15. The bioreactor chamber of claim 11, further comprising a media circulation path passing through the inlet cap, into the first inlet segment, through the perfusion core and the media channels positioned over the first inlet segment into the core of the sleeve, then through the media channels positioned over the second outlet segment into the central core of the perfusion core, and out through the outlet cap.

16. The bioreactor chamber of claim 11, wherein the width of the disk is 1-10% of the diameter of the disk.

17. The bioreactor chamber of claim 11, wherein the scaffold has numerous pores of various sizes that penetrate the scaffold.

18. The bioreactor chamber of claim 11, wherein the scaffold has multiple concavities spaced along a perimeter of the scaffold.

19. The bioreactor chamber of claim 18, wherein the concavities make up at least 50% of the perimeter of each scaffold and less than 15% of the surface of the disk.

20. The bioreactor chamber of claim 11, wherein the plurality of scaffolds are identical in size and shape.

21. The bioreactor chamber of claim 11, wherein each scaffold is coated with a peptide or a protein before the scaffold is assembled within the bioreactor chamber.

* * * * *